(12) United States Patent
Zhang et al.

(10) Patent No.: US 6,759,576 B2
(45) Date of Patent: Jul. 6, 2004

(54) ENHANCED POLLENIZER AND METHOD FOR INCREASING SEEDLESS WATERMELON YIELD

(75) Inventors: Xingping Zhang, Woodland, CA (US); Tom Vare Williams, Naples, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 10/091,154

(22) Filed: Mar. 5, 2002

(65) Prior Publication Data

US 2004/0060085 A2 Mar. 25, 2004

(51) Int. Cl.[7] .............................. A01H 5/00; A01H 1/00; A01H 5/10
(52) U.S. Cl. ...................................... 800/308; 800/260
(58) Field of Search ................................ 800/260, 308

(56) References Cited

U.S. PATENT DOCUMENTS

| | | |
|---|---|---|
| 6,355,865 B1 | 3/2002 | Elmstrom .................... 800/308 |
| 2003/0121075 A1 | 6/2003 | Barham ....................... 800/308 |
| 2003/0163852 A1 | 8/2003 | Barham et al. .............. 800/308 |

OTHER PUBLICATIONS

*Known–You Seed*, (Kaohsiung, Taiwan), [catalog], 1991/1992, pp. 22.
*Known–You Seed*, (Kaohsiung, Taiwan), [catalog], 1994, pp. 2.
Wolf et al., *Genetic Variability in Flower Attractiveness to Honeybees (Apis mellifera L.) within the Genus Citrullus HortScience*, vol. 34(5), (1999) pp. 860–863.
NeSmith, D.S. and Duval, J.R., *Fruit Set of Triploid Watermelons as a Function of Distance from a Diploid Pollinizer HortScience*, vol. 36(1) (Feb. 2001) pp. 60–61.
Hochmuth, et al. "Cultural Management." in Maynard, D.N., *Watermelons: Characteristics, Production, and Marketing* (Virginia, ASHA Press, 2001), pp. 78–97.
United States Department of Agriculture, Insect Pollination of Cultivated Crop Plants, Common Vegetables for Seed & Fruit; Watermelon and Cirton [online]. Originally pubished 1976 retrieved from the Internet: <URL: http://gears.tucson.ars.ag.gov/book/.
Kenny, I.J. and Porter, D.R., *Relative Rind Toughness Among Watermelon Varieties American Society for Horticultural Science*, vol. 38 (1941) pp. 537–540.
Poole, C.F., *Genetics of Cultivated Cucurbits The Journal of Heredity*, vol. 35 (1944) pp. 122–128.
Porter, D.R., *Inheritance of Certain Fruit and Seed Characters in Watermelons Hilgardia*, vol. 12, No. 10 (Jan., 1937) pp. 489–509.
Rhodes, B. and Dane, F, *Gene List for Watermelon Cucurbit Genetics Cooperative Report*, vol. 22 (1999) pp. 61–77.

*Primary Examiner*—Anne Kubelik
(74) *Attorney, Agent, or Firm*—Edouard G. Lebel; Bruce Vrana

(57) ABSTRACT

An enhanced, diploid pollenizer watermelon plant and method used to maximize the yield of triploid seedless watermelons per area. The enhanced pollenizer watermelon plant of the invention is either a hybrid variety, an open-pollinated variety or a synthetic variety, that exhibits the characteristics of lacy vine, small leaves, prolific male flowers, small fruit with a brittle rind that splits when the fruit is overripe or breaks when relatively small physical forces are applied. The watermelon plant of the invention is also characterized by extended flowering duration, thereby increasing the number of triploid watermelon flowers that are pollinated and set fruit. The method for producing a seedless watermelon fruit, includes the steps of providing a pollenizer diploid watermelon plant, extending the duration of flowering of the pollenizer plant while reducing the number of such plants needed to pollenize the same number of triploid watermelon plants, and maximizing dispersal of the pollenizer watermelon plant throughout the field of triploid watermelon plants.

24 Claims, 2 Drawing Sheets

ENHANCED POLLENIZER AND METHOD FOR INCREASING SEEDLESS WATERMELON YIELD

FIELD OF THE INVENTION

This invention is in the field of watermelon breeding, specifically relating to diploid watermelons used to pollinate triploid watermelon plants for the commercial production of seedless watermelon fruit, and includes a novel method for the production of triploid watermelon fruit.

BACKGROUND OF THE INVENTION

Watermelon is an important horticultural crop that accounts for 2% of the world area devoted to vegetable crops. There were 6,024,000 acres of watermelon grown in the world and 187,000 acres of watermelons grown in the United States in 1997 (FAO Production Yearbook 51, 1998). The estimated annual world watermelon value exceeded $7.6 billion when using the United States average price for 1995–1997. The United States watermelon crop amounted to over 41 million cwt, from over 174,000 harvested acres, and a farm value of over $266 million, accounted for 9.2% of the harvested acres, 10.0% of the production, and 3.5% of the value of the United States fresh vegetable industry in 1999 (USDA Agricultural Statistics 2001). California was the leading state in watermelon farm gate value, exceeded $72 million 2000, due to high percentage of triploid seedless watermelon grown in California Seedless watermelon receives well above the average price for seeded watermelons in the market.

The goal of plant breeding is to combine in a single variety or hybrid various desirable traits. Desirable traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, and maturity, are important. Other desired traits may include particular nutrient content, color, fruit shape, as well as taste characteristics.

As with many different plants, watermelon contains a fruit part and a plant part. Each part contains different traits that are desired by consumers and/or growers, including such traits as flavor, texture, disease resistance, and appearance traits such as shape and color. The seedless trait in the watermelon fruit is highly desired by consumers. For production of seedless watermelon, optimum pollination characteristics of the pollinating plant are desired.

Seedless watermelon plants are triploid and must be pollinated by the pollen of diploid watermelon plants. To provide adequate pollenization of seedless watermelon plants, it is current practice to plant diploid pollenizer plants over approximately 25–33% of the field surface. The remaining portion of the field is planted with the triploid plants. Thus, to maximize the value of the crop in the field, growers use high yield marketable diploid watermelon varieties, which ultimately compete with the triploid seedless varieties for sun, nutrients, and space. The present invention recognizes the need to increase the pollenizing capacity of diploid watermelon plants in order to decrease the ratio of diploid to triploid plants in the field, thereby increasing the yield of the seedless watermelon. The present invention further recognizes that the novel phenotypic characteristics of the diploid pollenizer plants of the invention permits these diploids to be planted in close proximity to the triploid plants and to share the field surface with the triploid plants, thereby effectively decreasing the surface area of the field required for the diploid pollenizers of the invention.

SUMMARY OF THE INVENTION

The present invention uses a novel diploid watermelon to improve current methods of commercial production of seedless watermelon and to increase seedless watermelon yield. According to the invention, there is provided a novel enhanced, pollenizer diploid watermelon (hereinafter referred to as "enhanced pollenizer") and method for pollinating seedless watermelon plants. The present invention includes an enhanced pollenizer having a high number of open (lacy) branches. The openness of the branched or lacy vine results, in part, from the distinct small and non-overlapping, deep lobed leaves. The lacy branches and small, non-overlapping, deep lobed leaves of the invention provide more access of bees to the flowers of both the pollenizing and the triploid plant, thereby enhancing transfer of the pollen from enhanced pollenizer watermelon to the female flowers of the triploid watermelon. A second advantage of small leaves characterized by deep, non-overlapping lobes is that more sunlight is able to penetrate to adjacent triploid plants. The third advantage of small leaves characterized by deep, non-overlapping lobes is that these leaves take up less field area than the substantially larger leaves of the diploid pollenizers currently used in the production of seedless watermelon.

Also according to the present invention, there is provided a novel enhanced pollenizer comprising small fruits with brittle rind. The small fruits with brittle rind reduce the load to the plant and allow the plant to continue flowering for extended periods of time, significantly greater than pollenizer watermelons that are currently used in the production of seedless watermelon. Longer flowering duration of the enhanced pollenizer, compared to traditional pollenizer diploid watermelons, results in increased fruit set and yield of seedless watermelon.

The present invention also includes an enhanced pollenizer fruit that weighs approximately in the range of 2 to 7 lbs.

The present invention further includes an enhanced pollenizer fruit rind that breaks under a pressure approximately in the range of 7–11 lbs/in$^2$.

The present invention includes an enhanced pollenizer having leaves with a surface area approximately in the range of 25–40 cm$^2$.

Also included in the invention is a enhanced pollenizer plant for pollinating triploid plants producing seedless watermelon fruit, comprising, at maturity, the characteristics of smaller fruit and leaf size compared to the watermelon variety Sangria™, deep, non-overlapping lobes, wherein the fruit rind is more brittle than the rind of the variety Sangria™.

The pollenizer diploid watermelon of the invention is further enhanced by including resistance to various pests and herbicides via conventional plant breeding methods or genetic transformation.

The present invention also provides a method for interplanting enhanced pollenizer plants amongst the triploid watermelon plants in a field in a pattern that decreases the ratio of pollenizing plants to triploid plants and increases the field surface for triploid plants.

Also included in the present invention is a method of increasing the yield of triploid, seedless watermelon comprising the steps of reducing fruit load of said enhanced pollenizer watermelon, increasing the flowering duration of said pollenizer watermelon, planting said enhanced pollenizer watermelon in a field of triploid watermelon; and harvesting said triploid watermelon.

The invention also a method of increasing the yield of triploid seedless watermelon plants by using small fruited, yet enhanced pollenizer watermelon plants wherein the fruit are not harvested for human consumption.

DETAILED DESCRIPTION OF THE INVENTION

Development of Seedless Watermelons

Figure 1:
FIG. 1 is a scanned image of a photographic depiction of a leaf of the enhanced pollenizer plant of the invention.

Triploid watermelons are created by crossing a tetraploid (4X) female line with diploid (2X) male line. The resulting triploid (3X) watermelon seed are planted in a field with diploid watermelon pollenizers. The resulting fruit of the triploid watermelon are seedless.

To create a tetraploid female watermelon line, it is known in the art to use chemicals that alter mitosis of a diploid inbred line so that unusual numbers of chromosomes are obtained. For example, colchicine is a chemical that alters the mitotic spindle fibers of diploid cells resulting in a number of cells that are tetraploid. The diploid line used to create a tetraploid is selected based on the traits desired for the tetraploid line. Traits that are desired for a tetraploid line may therefore first be introgressed into the diploid inbred lines that will be used to develop the tetraploid lines by breeding methods well known to those skilled in the art. Thus, the diploid and tetraploid parent lines are bred separately for the desired traits.

It usually requires at least two generations of self-pollination and selection to "fix" the 4X condition, after the colchicine treatment generation because, often, chromosomal aberrations are encountered that affect seed fertility, and must be eliminated. Once the stable tetraploid containing the desired characteristics is verified, it then can be used as a stable female parent for the production of the triploid hybrid. A stable diploid inbred is selected for use as the male parent. Methods for developing tetraploid plants are described in Kihara, H., 1951, Triploid Watermelons, *Proceedings of American Society for Horticultural Science* 58:217–230; and Eigsti, O. J., 1971, Seedless Triploids, HortScience 6, pgs. 1–2.

The tetraploid female and diploid male are planted in a seed production field. The pollen of the diploid male parent is transferred to the female tetraploid flower by methods well known to those skilled in the art. The triploid seed that is produced is present in the resulting fruit and is planted to produce the triploid plants. The breeding of watermelon is further described in Mark Bassett (Editor), 1986, Breeding Vegetable Crops, AVI Publishing, ISBN 0-87055-499-9.

A triploid seedless watermelon is a true F1 hybrid between a tetraploid watermelon, as the female p and a diploid watermelon, as the male parent (Kihara, H. 1951. Triploid Watermelons. *Proceedings of American Society for Horticultural Science* 58:217–230). The seedless condition in triploid watermelon is the result of the presence of three homologous sets of chromosome per somatic cell rather than the usual two. Cells with three sets of homologous chromosomes are said to be triploid and are designated as 3X. The triploid seedless watermelons have 33 chromosomes (2N=3X=33) in their somatic cells. The inability of the triploid zygote to produce normal viable gametes (pollen and egg cells) causes the absence of seeds in triploid fruits. Typically, seedless watermelons contain small edible white ovules, similar to those in immature cucumbers.

Adequate viable pollen supply from the diploid pollenizer watermelon is essential for the triploid female flowers to set and develop into regular seedless fruit. The female flowers of triploid watermelon will not set if they are not pollinated by viable pollen of diploid watermelon. (Maynard, D. N. (editor), 2001, *Watermelons: Characteristics, Production and Marketing*, ASHS Press, ISBN 0-9707546-1-2). The diploid watermelon grown in a field of triploid plants is referred to herein as the "pollenizer." In current commercial triploid watermelon production fields, the triploid watermelon and diploid pollenizer are inter-planted, either within row or between rows, in a ratio of approximately 1 diploid to 2 or 3 triploids. Although research has indicated a 1:4 ratio is acceptable, it is rarely used in commercial plots. (NeSmith, D. S., Duval, J. R. *Fruit Set of Triploid Watermelons as a Function of Distance from a Diploid Pollenizer*, HortScience 36(1): 60–61, 2001)

Development of Enhanced Pollenizer Diploid Watermelon

According to the present invention, a watermelon (OW824) is selected having the characteristics of a heavily branching lacy vine, early and prolific male flowers, small leaves with deep, non-overlapping leaf lobes. In this example, the fruit of OW824 is relatively large, the rind and flesh are very firm, the seed size is very big and the flesh is white.

Also according to the invention, a hybrid watermelon (OW823) is selected for its small fruit (2–3 kg) with brittle rind that splits easily. 0W823 also includes the characteristics of mid-sized seeds with yellow flesh. Crossing OW824× 0W823 generated progeny having the characteristics of the enhanced pollenizer diploid watermelon of the present invention as described in more detail below.

The initial cross of OW824×OW823 was made during the summer of 2000 in California The $F_1$ generation was grown in the greenhouse in the fall of 2000. The $F_2$ population was grown Florida in the spring, and in California in the summer of 2001. Individuals with the set of traits required for the enhanced pollenizer were successfully identified and self-pollinated in $F_2$ populations grown in both locations. A total 7 selections were made. The 7 $F_3$ lines were grown in the field in Florida and the greenhouse in California in the fall of 2001 for further selection and evaluation. Three $F_3$ lines were identified to best meet our breeding goals and advanced to $F_4$ generation. They all have the set of the traits required by the enhanced pollenizer. One line, NO1F3203B is fixed for every trait concerned. NO1F3203B contains the traits that are illustrative of the traits of the enhanced pollenizer of the invention.

Leaf: The leaves of the enhanced pollenizer are significantly smaller with deep, non-overlapping leaf lobes and are more numerous than that of the commonly used pollenizers such as the variety Sangria# (See FIGS. 1 and 2). The leaf surface areas of the enhanced pollenizer NO1F3203B and the Sangria™, a pollenizer favored by growers, are shown for comparison purposes in Table 1. The leaves for both NO1F3203B and Sangria™ were taken from mature plants sowed on Aug. 20, 2001 and harvested on Nov. 8, 2001.

TABLE 1

| NO1F3203B LEAF | cm² | SANGRIA LEAF | cm² |
|---|---|---|---|
| A | 38.75 | A | 232.00 |
| B | 26.25 | B | 447.25 |
| C | 39.75 | C | 241.50 |
| D | 28.75 | D | 238.00 |
| E | 38.25 | E | 211.00 |
| F | 26.27 | | |
| | 33.08 (±6.46) | | 273.95 (±97.60) |

The surface area of the enhanced pollenizer leaf of the invention is approximately 5 to 12 times less than the surface area of the typical diploid pollenizer, Sangria™ plant.

Figure 2:
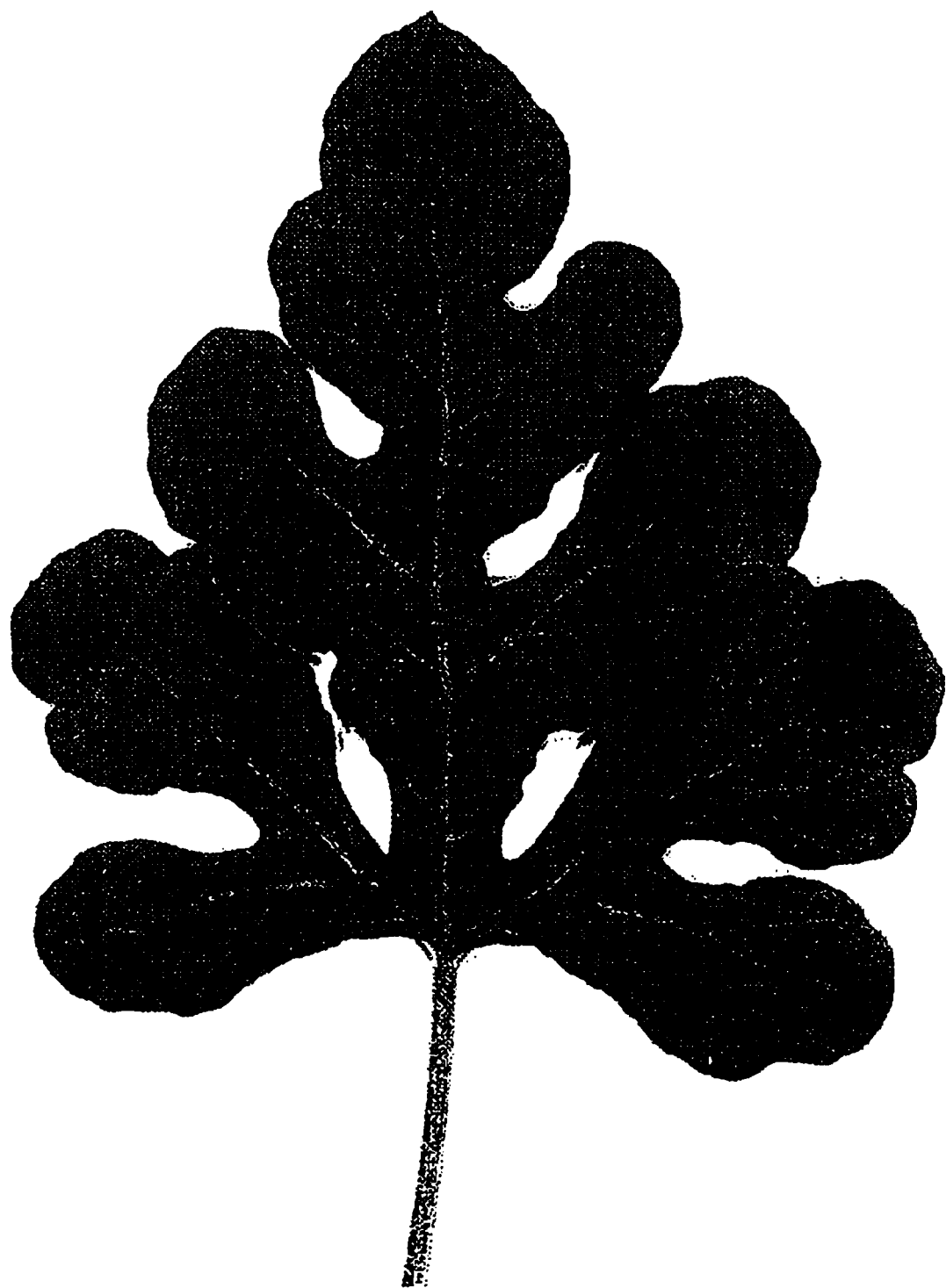
FIG. 2 is a scanned image of a photographic depiction of a leaf of the pollenizer referred to as Sangria™ that is currently used in commerce.

FIG. 1 illustrates the non-overlapping characteristic of the deep, non-overlapping lobed leaves of the enhanced pollenizer. Clearly, due to various environmental and physical forces, some of the leaves in this population may have some overlapping lobes, but overlapping lobes are not characteristic thereof. In contrast, the Sangria™ leaf shown in FIG. 2 is characterized as having leaf lobes that habitually overlap each other. The small, deeply lobed and non-overlapping leaves of the invention allow more sunlight through to adjacent triploid watermelon plants.

Branching: The enhanced pollenizer of the invention is also heavily branched (also referred to as "lacy vined"), having significantly more branches (average of 25.9) than the variety referred to as Sangria™, (average of 13). The lacy vine characteristic enables the enhanced pollenizer to produce more accessible male flowers, thereby enhancing exposure of the flowers to bees.

Fruit: The fruit rind of the enhanced pollenizer is very brittle and is easily broken. The brittle fruit rind splits easily, due to maturation or by breaking or splitting of the fruit during harvest of the seedless triploid watermelon. Splitting of fruit signals the plant that it hasn't completed its reproductive process inducing the plant to continue flowering for a longer period of time. Brittleness is conferred by a gene e (explosive rind, thin, and tender rind, bursting when cut (Rhodes & Dane, 1999, Gene List for Watermelon, Cucurbit Genetics Cooperative Report 22:71–77). When measured by a penetrometer, the NO1F3203B breaks at about 7–11 lbs/in², whereas a typical watermelon such as Sangria™ breaks at about 21–27 lbs/ in².

The fruit size of the enhanced pollenizer is approximately 6 inches long×7 inches wide, whereas the typical pollenizer is about 10 inches long×20 inches wide. Small fruit size, as well its brittleness was selected to decrease the load on the plant, thereby extending the duration of plant growth and flower production. Another advantage of the small fruit size is that it enables the harvester to easily distinguish the seedless fruit from seeded fruit, is often difficult with currently used pollenizers, which are selected based on their overall similarity to the seedless triploid plants.

Flowering: The plants of NO1F3203B also flower approximately 7 to 10 days earlier than diploid pollenizer plants currently used for the production of seedless watermelon, and continue flowering during fruit harvest time of the seedless watermelon, 2 to 3 weeks longer than standard diploid pollenizer plants. Thus, the pollenizer plant of the invention has a flowering duration that is approximately 3 to 5 weeks longer than pollenizers currently used.

Other Traits: NO1F3203B can be used either as donor of the set of traits disclosed above, or as the recurrent parent to develop additional enhanced pollenizer lines. In accordance with the invention, the enhanced pollenizer watermelon contains traits of disease resistance (e.g. Fusarium wilt, Anthracnose, Gummy Stem Blight, Powdery Mildew, and Bacterial Fruit Blotch), insect resistance (e.g. cucumber beetle, aphids, white flies and mites), salt tolerance, cold tolerance and/or herbicide resistance added. These traits can be added to existing lines by using either conventional backcrossing method, pedigree breeding method or genetic transformation. The methods of conventional watermelon breeding are taught in several reference books, e.g. Maynard, D. N. (editor), 2001, WATERMELONS Characteristics, Production and Marketing, ASHS Press; Mohr, H. C., Watermelon Breeding, in Mark J. Bassett (editor), 1986, Breeding Vegetable Crops, AVI Publishing Company, Inc. General methods of genetic transformation can be learned from publish references, e.g. Glich et al., (Eds), 1993, Methods in Plant Molecular Biology & Biotechnology, CRC Press.

Forms of the Enhanced Diploid Pollenizer: Once the enhanced pollenizer lines are developed, several forms of enhanced pollenizer varieties can be used in commercial seedless watermelon production. Specifically, these forms of enhanced pollenizer varieties include:

Forms of Enhanced Pollenizer. (1) Open Pollinated Variety: The stable, enhanced lines of the enhanced pollenizer are grown in isolated fields, at least 2,000 meters from other watermelon varieties. Pollination is conducted in the open fields by bees. Seeds are harvested from the seed production field when the fruit and seeds are fully developed. The seeds are dried and processed according to the regular watermelon seed handling procedures. (2) Synthetic Variety: The seed of different enhanced pollenizer lines are individually produced in isolated fields. Bee pollination is used in each isolation. The seed of different enhanced pollenizer are separately harvested and processed. Mixing several enhanced pollenizer lines in various ratios forms the synthetic varieties. The synthetic variety can provide a broader pollenizer population for the triploid watermelons. (3) Open-Pollinated Hybrid Variety: Two or several enhanced pollenizer lines are planted in the same seed production field with bee pollination. The harvested seed lot, therefore, contains both hybrid and inbred seed. (4) Hybrid Variety: Two enhanced pollenizer lines, the male and female parents, are planted in the same field. Hand pollination is conducted. Only the seed from female parent line is harvested and sold to the commercial grower to use as pollenizer.

Method of Seedless Watermelon Production: Most current commercial seedless watermelon growers in NAFTA use elongated diploid varieties with an Allsweet stripe pattern: light green skin with wide green stripes, as the pollenizer. The variety referred to as Sangria™ is the most preferred Allsweet type pollenizer and is available as a commercial product from Syngenta Seeds, Inc., Boise Id. Typically, the pollenizer is inter-planted with the triploid watermelon either between rows or within row. The current method of planting diploid pollenizers include planting the diploid plants at a distance from adjacent triploid such that they have the same field area available per plant as the field area that is available to the triploid watermelon plants. For example, currently watermelon growers inter-plant the diploids within a row, whereby the space between all adjacent plants within the row are approximately equidistant.

Alternatively, diploid pollenizer plants are planted in separate rows between rows of triploid watermelon plants. All rows of diploid and triploid plants in such a field are planted approximately equidistant from each other. In other words, under current methods for producing seedless watermelon, the width of all diploid and triploid rows is the same.

The method of the present invention includes planting the enhanced pollenizer watermelon plants in rows that are narrower than the triploid rows, thereby saving field area for production of triploid seedless watermelon.

EXAMPLE 1

Triploid watermelon plants are planted in parallel rows 7 feet apart and 3 feet apart within each row. However, the enhanced diploid watermelon plants are planted in a narrow row 3.5' wide (½ the width of the triploid rows) between every second and third triploid row. For example, rows A and B are two consecutive rows of triploids, each 7-foot wide. Row C is a diploid row that is 3.5 feet wide. Row D and E are the following two 7 foot wide rows of triploids, followed by the 3.5-foot wide row F of diploid plants. This pattern is repeated across the width of the field. Because the diploid row is narrower according to the method of the invention, the distance between rows B and D is 10.5 feet instead of the traditional distance of 14 feet Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

EXAMPLE 2

Triploid watermelon plants are again planted in parallel rows 7 feet apart and 3 feet apart within each row. As in Example 1, the enhanced diploid watermelon plants are planted in a narrow row 3.5' wide, but are planted between every third and fourth triploid row. For example, rows A, B, and C, are three consecutive rows of triploids, each row being 7' wide. The following row D is a diploid row that is 3.5 feet wide. Row E, F, and G are the following three rows of triploids, all 7 feet wide, followed by a 3.5 foot wide row of enhanced pollenizer plants. This pattern is repeated across the width of the field. Because the diploid row is narrower according to the method of the invention, the distance between rows B and D is again 10.5 feet instead of the traditional distance of 14 feet. Using this ratio of 1 pollenizer row for every 3 triploid rows (1:3), 25% of the field would normally be used for the pollenizer plants. Reducing the width of the pollenizer row according to the method of the invention by one-half, the gain of space for planting additional triploid plants would be 25%/2 or approximately 12%.

EXAMPLE 3

Triploid watermelons are planted in parallel rows 8 feet apart and 3 feet apart within each row. The enhanced diploid watermelon plants are planted in a narrow row 4.0 feet wide (½ the width of the triploid rows) between every second and third triploid row. For example, rows A and B are two consecutive rows of triploids, each 8 foot wide. Row C is a diploid row that is 4.0 feet wide. Row D and E are the following two 8 foot wide rows of triploids, followed by the 4.0 foot wide row F of diploid plants. This pattern is r ed across the width of the field. Because the diploid row is narrower according to the method of the invention, the distance between rows B and D is 12.0 feet instead of the traditional distance of 16 feet. Using this ratio of 1 pollenizer row for every 12.0 triploid rows (1:2), 33.3% of the field would normally be used for the pollenizer plants. Reducing the width of the pollenizer row according to the method of the invention by one-half the gain of space for planting additional triploid plants would be 33.3%/2 or approximately 17%.

EXAMPLE 4

Referring to the above three examples, when triploids are planted in rows 8 feet apart, and the ratio of diploid to triploid is 1:3, it is now clear that the reduction of the pollenizer row width by one-half will gain space for planting additional 12%.

EXAMPLE 5

It is also within the scope of the invention to reduce the pollenizer row width to approximately ⅓ that of the triploid row width. Thus, according to the present invention, at any row width, when the ratio of diploid rows to triploid rows is:
  (a) 1:2, the savings of field area for additional triploid plants is (33%×⅔) or 22%.
  (b) 1:3, the savings of field area for additional triploid plants is (25%×⅔) or 16.5%.
  (c) 1:4, the savings of field area for additional triploid plants is (20%×⅔) or 13.2%.

It is also within the scope of the invention to reduce the pollenizer row width to approximately ⅔ that of the triploid row width.

EXAMPLE 6

It is also within the scope of the present invention to inter-plant the diploid plants within the rows of triploid plants. According to the invention, the triploid plants are first planted by machine or by hand in regularly spaced rows. The triploid plants within each row are planted, for example, 3 feet apart. After the triploid plants are in the field as described, the diploid pollenizer watermelon plants of the invention are inter-planted, by hand, within each row approximately midway between the triploid plants. Thus, in this example, the diploid plants are planted approximately lot feet from the flanking triploid plants within the row. Due to the characteristics of the enhanced pollenizer of the invention, the diploid plants can be inter-planted within each row after every 2, 3, 4, 5, 6, 7, 8, 9, or 10 consecutive triploid plants. It is currently preferred in the industry to plant the diploid plants after every 2 (1:2) or 3 (1:3) triploid plants within the row. A 1:4 ratio has been reported, but is not normally used in commercial fields due to inadequate pollenization of the triploid plants. The field area saved under this example, when compared with both the current methods of planting diploids in separate rows or within a row at the ratios (diploid:triploid) of:
  (a) 1:2, is 33.3%,
  (b) 1:3, is 25%,
  (c) 1:4, is 20%.

The enhanced pollenizer and method of the present invention comprises planting the enhanced pollenizer watermelons in rows that are narrower than the rows containing the triploid plants. Although the narrower diploid row will encourage diploid plant growth into the triploid plant row, the novel characteristics of the enhanced pollenizer watermelon allow it maintain its ability to sufficiently pollinate the triploid plants in the field. Thus, the enhanced pollenizer watermelon and method of the present invention increase the yield of seedless watermelon in a field.

Deposit

Applicants have made a deposit of at least 2500 seeds of enhanced watermelon pollenizer line NO1F3203B with the American Type Culture Collection (ATCC), Manassas, Va., 20110-2209 U.S.A., ATCC Deposit No: PTA-4856. This deposit of the enhanced watermelon pollenizer line NO1F3203B will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restriction imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims. Thus, although the foregoing invention has been described in some detail in this document, it will be obvious that changes and modification may be practiced within the scope of the invention, as limited only by the scope of the appended claims.

What is claimed is:

1. Seed of diploid watermelon line NO1F3203B, wherein representative seed of said line is having been deposited under ATCC Accession No: PTA-4856.

2. A diploid watermelon plant of line NO1F3203B, wherein representative seed of said line is having been deposited under ATCC Accession No: PTA-4856.

3. Pollen of the plant of claim 2.

4. An ovule of the plant of claim 2.

5. Fruit of the plant of claim 2, wherein the fruit is produced by self-pollination of the plant.

6. A method for producing triploid, seedless watermelon fruit, wherein the method comprises the steps of:
   a) planting a field with rows of triploid watermelon plants;
   b) inter-planting a diploid watermelon plant according to claim 2 within said rows of triploid watermelon plants after every $2^{nd}$, $3^{rd}$, $4^{th}$, $5^{th}$, $6^{th}$, $7^{th}$, $8^{th}$, $9^{th}$, or $10_{th}$ triploid plants;
   c) allowing pollination of said triploid watermelon plants by pollen of said diploid watermelon plant to obtain triploid, seedless watermelon fruit; and
   d) harvesting said triploid, seedless watermelon fruit.

7. A method for producing triploid, seedless watermelon fruit, wherein the method comprises the steps of:
   a) planting a field with rows of triploid watermelon plants;
   b) planting said field with rows of diploid watermelon plants according to claim 2, wherein the rows of diploid watermelon plants are approximately one-third to two-thirds the width of the rows of triploid watermelon plants; and
   c) allowing pollination of said triploid watermelon plants by pollen of said diploid watermelon plants to obtain triploid, seedless watermelon fruit.

8. The method for producing triploid, seedless watermelon fruit according to claim 7, wherein the rows of diploid watermelon plants are approximately one-half to two-thirds the width of the rows of triploid watermelon plants.

9. The method for producing triploid, seedless watermelon fruit according to claim 7, wherein said rows of diploid watermelon plants are planted after every two rows of triploid watermelon plants.

10. The method for producing triploid, seedless watermelon fruit according to claim 7, wherein said rows of diploid watermelon plants are planted after every three rows of triploid watermelon plants.

11. The method for producing triploid, seedless watermelon fruit according to claim 7, wherein said rows of diploid watermelon plants are planted every four rows of triploid watermelon plants.

12. The method for producing triploid, seedless watermelon fruit according to claim 7, further comprising harvesting said triploid, seedless watermelon fruit.

13. The method for producing triploid, seedless watermelon fruit according to claim 7, wherein the rows of diploid watermelon plants are approximately one-third to one-half the width of the rows of triploid watermelon plants.

14. A method of increasing the yield of triploid, seedless watermelon plants, wherein the method comprises the steps of:
   a) obtaining the diploid watermelon plants according to claim 2 for pollenizing said triploid, seedless watermelon plants;
   b) planting said diploid watermelon plants in a field of triploid watermelon plants;
   c) allowing pollination of said triploid watermelon plants by pollen of said diploid watermelon plants to obtain triploid, seedless watermelon fruit; and
   d) harvesting said triploid, seedless watermelon fruit.

15. The method of increasing the yield of triploid, seedless watermelon plants according to claim 14, wherein planting of said diploid watermelon plants is at a ratio of approximately equal to or less than 1 diploid watermelon plant to 2 triploid, seedless watermelon plants.

16. The method of increasing the yield of triploid, seedless watermelon plants according to claim 14, wherein planting of said diploid watermelon plants is at a ratio of approximately equal to or less than 1 diploid watermelon plant to 4 triploid, seedless watermelon plants.

17. A method for producing seeds of a watermelon plant, wherein the method comprises the steps of:
   a) growing in a field the watermelon plant according to claim 2;
   b) conducting pollination of said plant; and
   c) harvesting seed of said plant.

18. The method according to claim 17, further comprising drying said seed.

19. A method for producing a hybrid watermelon variety, wherein the method comprises the steps of:
   a) planting in a field a first and a second watermelon plant, wherein said first watermelon plant is the male parent, wherein said second watermelon plant is the female parent, and wherein said first or said second watermelon plant is the watermelon plant according to claim 2;
   b) conducting pollination between said first and second watermelon plants; and
   c) harvesting seed from said female parent, wherein said seed is seed of a hybrid watermelon variety.

20. A method for producing triploid, seedless watermelon fruit, wherein the method comprises the steps of:
   a) interplanting a diploid watermelon plant according to claim 2 and triploid watermelon plants in a field; and
   b) allowing pollination of said triploid watermelon plants by pollen of said diploid watermelon plant to obtain triploid, seedless watermelon fruit.

21. The method for producing triploid, seedless watermelon fruit according to claim 19, further comprising harvesting said triploid, seedless watermelon fruit.

22. A method for producing triploid, seedless watermelon fruit, wherein the method comprises the steps of
   a) interplanting seed of a diploid watermelon line according to claim 1 and triploid watermelon plants in a field;
   b) allowing said seed to grow into diploid watermelon plants; and
   c) allowing pollination of said triploid watermelon plants by pollen of said diploid watermelon plants to obtain triploid, seedless watermelon fruit.

23. A method for producing triploid, seedless watermelon fruit, wherein the method comprises the steps of
   a) interplanting diploid watermelon plants according to claim 2 and seed of triploid watermelon plants in said field;
   b) allowing said seed to grow into triploid watermelon plants; and
   c) allowing pollination of said triploid watermelon plants by pollen of said diploid watermelon plants to obtain triploid, seedless watermelon fruit.

24. A method for producing triploid, seedless watermelon fruit, wherein the method comprises the steps of
   a) interplanting seed of a diploid watermelon line according to claim 1 and seed of triploid watermelon plants in a field;
   b) allowing said seed to grow into diploid watermelon plants and triploid watermelon plants, reaspectively; and
   c) allowing pollination of said triploid watermelon plants by pollen of said diploid watermelon plants to obtain triploid, seedless watermelon fruit.

* * * * *

UNITED STATES PATENT AND TRADEMARK OFFICE
CERTIFICATE OF CORRECTION

PATENT NO. : 6,759,576 B2 Page 1 of 1
APPLICATION NO. : 10/091154
DATED : July 6, 2004
INVENTOR(S) : Zhang et al.

It is certified that error appears in the above-identified patent and that said Letters Patent is hereby corrected as shown below:

In claim 1, at line 30, delete "having been"

In claim 2, at line 33, delete "having been"

In claim 6, at line 44, delete "$10_{th}$" and insert therefor --$10^{th}$--

Signed and Sealed this

Twenty-eighth Day of November, 2006

JON W. DUDAS
*Director of the United States Patent and Trademark Office*